United States Patent [19]

Akiba et al.

[11] Patent Number: 5,258,297
[45] Date of Patent: Nov. 2, 1993

[54] PROTEINASE-RESISTANT CELLULASE, MICROORGANISM PRODUCING THE SAME AND PROCESS FOR PRODUCING THE SAME

[75] Inventors: Shun-ichi Akiba; Akira Takei; Hiroshi Hagihara; Tomomi Ota; Hiroshi Kodama; Yoshiharu Kimura, all of Hasaki, Japan

[73] Assignee: Kao Corporation, Tokyo, Japan

[21] Appl. No.: 692,722

[22] Filed: Apr. 29, 1991

[30] Foreign Application Priority Data

May 24, 1990 [JP] Japan .................. 2-132659

[51] Int. Cl.$^5$ .......................... C12N 9/42; C12N 9/24
[52] U.S. Cl. ...................... 435/209; 435/200
[58] Field of Search ................ 435/209, 200

[56] References Cited

U.S. PATENT DOCUMENTS 4,943,532 7/1990 Kawai et al. ............... 435/209

FOREIGN PATENT DOCUMENTS 339550 11/1989 European Pat. Off.

OTHER PUBLICATIONS

Derwent Publication Limited, London, GB; Database WPIL, Accession No. 87-053000, Week 8708; & JP-A-62007795 [kao corp] Jan. 14, 1987.
Derwent Publication Limited, London GB; Database WPIL, Accession No. 86-314274, Week 8648; & JP-A-61231094 [Lion corp.] Oct. 15, 1986.

Primary Examiner—Douglas W. Robinson
Assistant Examiner—L. Blaine Lankford
Attorney, Agent, or Firm—Oblon, Spivak, McClelland, Maier & Neustadt

[57] ABSTRACT

A proteinase-resistant cellulase, a microorganism producing the same, and a process for producing such a proteinase-resistant cellulase is disclosed. The cellulase can be used as an additive to detergent compositions for washing clothes containing a proteinase, without immobilization or stabilization by chemical modification. The proteinase-resistant cellulase can be produced by a novel microorganism, *Aspergillus niger* KSM-24 [deposited with Fermentation Research Institute, Agency of Industrial Science and Technology (FERM BP-3359)].

1 Claim, 4 Drawing Sheets

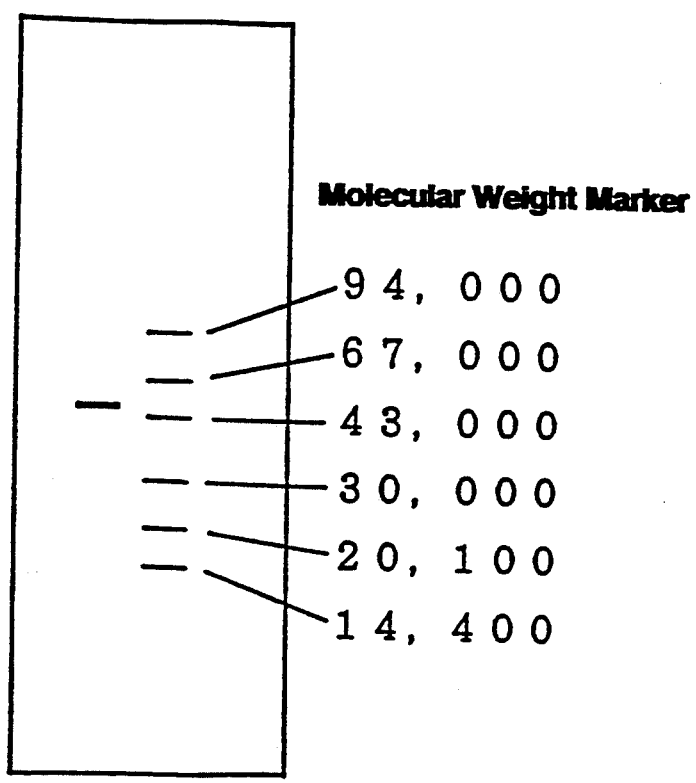

PROTEINASE-RESISTANT CELLULASE, MICROORGANISM PRODUCING THE SAME AND PROCESS FOR PRODUCING THE SAME

BACKGROUND OF THE INVENTION

1. Field of the Invention

This invention relates to a proteinase-resistant cellulase, a microorganism producing the same, and a process for producing such a proteinase-resistant cellulase.

2. Description of the Background

Conventionally, studies on cellulose-decomposable enzymes (cellulases) have been undertaken for the purpose of effective utilization of biomass resources. Examples of cellulases heretofore reported include those derived from molds belonging to the genera Trichoderma, Aspergillus, Acremonium, Humicola; bacteria belonging to the genera Pseudomonas, Cellulomonas, Ruminococcus, Bacillus; and ray fungi belonging to the genera Streptococcus, Actinomyces; and the like. At the present time, however, few cellulases utilizing biomass resources are produced in an industrial scale.

In the area of utilization of cellulases, on the other hand, the application of cellulases as an additive to detergents for washing clothes is lately on the increase (Japanese Patent Publication (kokoku) Nos. 49279/1984, 23158/1985, 36240/1985, etc.). Several processes are known for producing alkaline cellulases which can be used as a component of detergent compositions for washing clothes. Such processes include a process for collecting cellulase A by culturing an alkalophilic microorganism belonging to the genus Bacillus (Japanese Patent Publication (kokoku) No. 28515/1975), a process for producing alkaline cellulase 301-A by culturing an alkalophilic microorganism belonging to the genus Cellulomonas (Japanese Patent Laid-open (kokai) No. 224686/1983), a process for obtaining carboxymethyl cellulase (CMC) by culturing an alkalophilic microorganism, Bacillus sp. No. 1139 [Horikoshi et al.; J. Gen. Microbiol., 131, 3339 (1985)], a process for producing an alkaline cellulase with the use of a microorganism belonging to the genus Streptomyces (Japanese Patent Laid-open (ko-kai) No. 19483/1986), and a process for producing alkaline cellulase K by the culture of Bacillus sp. KSM-635 which is also a species of alkalophilic microorganisms (Japanese Patent Laid-open (ko-kai) No. 109776/1988). Beside these processes for producing alkaline cellulases, there are reports for the production of alkali-resistant cellulases such as alkali-resistant cellulases K-522 and K-588 (Japanese Patent Laid-open (ko-kai) Nos. 37285/1989 and 37286/1989).

All these cellulases, however, are not proteinase-resistant, and thus can not be incorporated in detergent compositions for washing clothes containing a proteinase. The means to overcome this problem such as the immobilization of a cellulase or the stabilization of a cellulase by chemical modification are not appropriate to industrial application because of the cost involved and the poor yields which can be achieved.

The development of cellulases which are inherently proteinase-resistant and are suitable for use as a component of detergent compositions for washing clothes is therefore desired.

In view of this situation, the present inventors have undertaken extensive studies in order to overcome the above problems and to obtain microorganisms capable of producing proteinase-resistant cellulases, and, as a result, discovered a cellulase which satisfies the above requirements among cellulases produced by specific microorganisms belonging to the genus Aspergillus.

SUMMARY OF THE INVENTION

Accordingly, an object of this invention is to provide novel proteinase-resistant cellulases, a microorganism producing the same, and a process for producing such proteinase-resistant cellulases.

In a specific embodiment of the present invention, a proteinase-resistant cellulase is provided which maintains the residual activity of 50% or more after two weeks when stored at 40° C. in the presence of 1 AU/ml proteinase.

As a preferred embodiment, the present invention provides a proteinase-resistant cellulase having the following physicochemical characteristics, (1) Action Exhibits significant activity on carboxymethyl cellulose (CMC) and dissolves CMC while producing reducing sugars.

(2) Substrate specificity

Beside CMC, exhibits some degree of activity on phosphoric acid-swollen cellulose and amilose.

(3) Working pH range and optimum pH

Has a working pH range of 3–10 and an optimum pH of 6.

(4) Stable pH range

Remains active when allowed to stand at 30° C. for 1 hour in a pH range of 3–11.

(5) Working temperature range and optimum temperature

Works in a wide temperature range of 20°–85° C., with the optimum temperature being 70° C.

(6) Temperature stability

Maintains a substantially all activity when allowed to stand at 60° C. for 10 minutes and 50% or more activity when allowed to stand at 75° C. for 10 minutes.

As a more preferred embodiment, the present invention provides a proteinase-resistant cellulase having the following physicochemical characteristics, (7) Effects of chelating agents The activity is not inhibited by EDTA, EGTA, NTA, and STPP.

(8) Effects of metallic ion

The activity is inhibited by $Cu^{2+}$, $Sn^{2+}$, and $Hg^{2+}$.

(9) Molecular weight

Has a molecular weight of about 60,000 measured by the gel permeation method.

(10) Sugar content

Contains 8% or more of sugars when measured by the phenol-sulfuric acid method.

(11) Resistance to surface active agents

Maintains the residual activity of 50% or more after two weeks when stored at 40° C. together with a 10% aqueous solution of linear alkylbenzene sulfonic acid, sodium alkylbenzene sulfonate, sodium alkyl sulfate, or sodium polyoxyethylenealkyl sulfate.

Another object of the present invention is to provide a microorganism named Aspergillus niger KSM-24 [deposited with Fermentation Research Institute, Agency of Industrial Science and Technology (FERM BP-3359)] and capable of producing a proteinase-resistant cellulase.

Still another object of the present invention is to provide a process for producing a proteinase-resistant cellulase comprising culturing a proteinase-resistant cellulase producing-microorganism belonging to the genus Aspergillus and collecting the proteinase-resistant cellulase from the culture broth.

Other objects, features and advantages of the invention will hereinafter become more readily apparent from the following description.

BRIEF DESCRIPTION OF THE DRAWING

FIG. 5 shows the results of the SDS-polyacrylamide gel electrophoresis of the proteinase-resistant cellulase.

DETAILED DESCRIPTION OF THE INVENTION AND PREFERRED EMBODIMENTS

Figure 1:
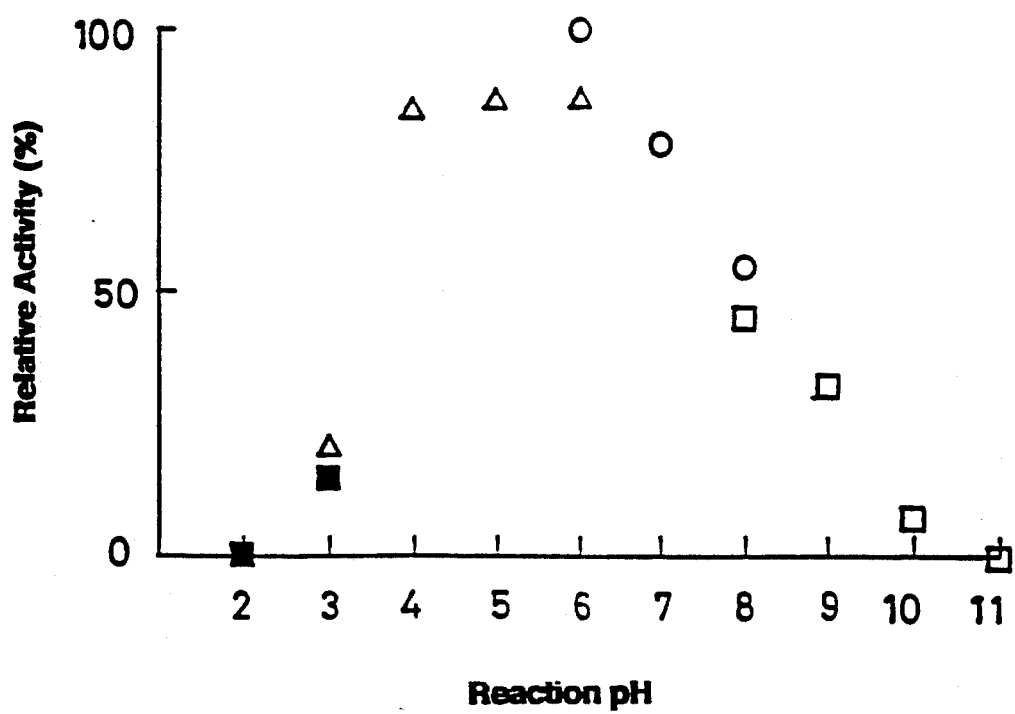
FIG. 1 is a graph showing the relationship between the enzymatic reaction pH and the relative activity of the proteinase-resistant cellulase of the present invention measured in a glycine-NaOH buffer solution (open squares), a sodium citrate buffer solution (open triangles), a sodium phosphate buffer solution (open circles), and a glycine-HCl buffer solution (solid squares).

*Aspergillus niger* IFO-31125 [IFO List of Cultures; eighth edition, Vol. 1 (1988); Institute of Fermentation, Osaka] and *Aspergillus niger* KSM-24 and *Aspergillus niger* KSM-25 discovered and isolated by the present inventors from the soil in Kashima-gun, Ibaragi-ken, Japan are given as examples of microorganism capable of producing proteinase-resistant cellulase according to the present invention. *Aspergillus niger* KSM-25 and *Aspergillus niger* KSM-24 possess the following mycological characteristics.

Mycological characteristics of *Aspergillusus niger* KSM-24

(a) Morphological characteristics

Myceria: have a diameter of about 2 μm, with a septum.
Conidiophoroe: have a diameter of about 6-8 μm, with a smooth surface.
Vesicle: the terminal of the conidiophoroe grows to form vesicle. The vesicle is spherical with a diameter of about 22-32 μm.
Sterigma: Sterigmas attach to the whole surface of the vesicle in two rows; the first and second sterigmas. The first sterigma is about 23-25 μm long and the second sterigma 5-6 μm long.
Conidia: Black sphere with about 1.6-2 μm diameter and smooth surface.
Conidium head: spherical or radial in shape.

(b) Growth in various culture media

1) Malt extract-agar medium: The colony has an irregular shape, 2-4 mm thick, with a convex center. The upper surface is black and the rear surface is white. The colony growth rate is 0.83 cm/day.
2) Potato-fructose-agar medium: The colony has an irregular shape, 2-4 mm thick, with a convex center. The growth of cells is excellent. The upper surface is black and the rear surface is white. The colony growth rate is 0.43 cm/day.
3) Czapek-agar medium: The colony has an irregular shape, 2-3 mm thick, with a slightly convex center. The upper surface is black and the rear surface is white. The colony growth rate is 0.83 cm/day.
4) Sabouraud-agar medium: The colony has a circular shape, 2-4 mm thick, with a convex swirl. The upper surface is black and the rear surface is white. The colony growth rate is 0.83 cm/day.
5) Automeal-agar medium: The colony is a circular disk, with a thickness of 1-2 mm. The cells grow well producing water drops. The upper surface is black and the rear surface is white. The colony growth rate is 1.10 cm/day.
6) YpSs-agar medium: The colony is a circular disk, with a thickness of 1-2 mm. The upper surface is black and the rear surface is white. The colony produces a yellow colored substance. The colony growth rate is 1.10 cm/day.

(c) Physiological and ecological characteristics

1) Growth pH: pH 4-10
2) Growth temperature: 20°-40° C.
3) Growth NaCl concentration: below 3 M.
4) Optimum pH: pH 5-6
5) Optimum temperature: 30° C.
6) Utilization of nitric acid: Positive
7) V-P test: Negative Mycological characteristics of *Aspergillus niger* KSM-25

(a) Morphological characteristics

The terminal of the conidiophoroe grows to form vesicle. Sterigmas attach to the whole surface of the vesicle in rows; Spores are spherical in shape and form long spherical or radial chains from top of the sterigmas.

(b) Growth in various culture media when cultured in each medium at 30° C. for 8 days.

1) Malt extract-agar medium: The colony has an irregular shape, 2-4 mm thick, with a convex center. The upper surface is black and the rear surface is white. The colony growth rate is 0.83 cm/day.
2) Potato-fructose-agar medium: The colony has an irregular shape, 2-4 mm thick, with a convex center. The growth of cells is excellent. The upper surface is black and the rear surface is white. The colony growth rate is 0.43 cm/day.
3) Czapek-agar medium: The colony has an irregular shape, 2-3 mm thick, with a slightly convex center. The upper surface is black and the rear surface is white. The colony growth rate is 0.83 cm/day.
4) Sabouraud-agar medium: The colony has a circular shape, 2-4 mm thick, with a convex swirl. The upper surface is black and the rear surface is white. The colony growth rate is 0.83 cm/day.
5) Automeal-agar medium: The colony is a circular disk, with a thickness of 1-2 mm. The cells grow well producing water drops. The upper surface is black and the rear surface is white. The colony growth rate is 1.10 cm/day.
6) YpSs-agar medium: The colony is a circular disk, with a thickness of 1-2 mm. The upper surface is black and the rear surface is white. The colony produces no yellow (c) Physiological and ecological characteristics 1) Growth pH: pH 4-10

2) Growth temperature: 20°–40° C.
3) Growth NaCl concentration: below 3 M.
4) Optimum pH: pH 5–6
5) Optimum temperature: 30° C.
6) Utilization of nitric acid: Positive
7) V-P test: Negative Based on the above mycological characteristics, the strains of the present invention were examined referring to *Classification and Identification of Microorganisms*, Vol. 1 (T. Hasegawa, Gakkai Press Center Co.) and *Separation, Culture and Identification of Fungi* (T. Udagawa and T. Muroi, Ishiyaku Publishing Co.), and determined as microorganisms belonging to *Aspergillus niger*. Since, however, the above mycological characteristics of the strains of the present invention are not identical with those of known *Aspergillus niger* microorganisms, the two microorganisms were judged to be novel and named *Aspergillus niger* KSM-24 and *Aspergillus niger* KSM-25. They were deposited with Fermentation Research Institute, Agency of Industrial Science and Technology (Deposition Nos. FERM BP-3359 and FERM BP-3360, respectively).

The production of proteinase-resistant cellulase using the proteinase-resistant cellulase-producing microorganisms belonging to the genus Aspergillus typified by the above two strains can be carried out by culturing the microorganism in a solid or liquid medium according to a conventional culture method and collecting the enzyme from the culture broth.

Inclusion of a suitable amount of carbon and nitrogen sources which the microorganism can utilize in the medium is desirable. There are no specific limitations as to the carbon and nitrogen sources. Enumerated as nitrogen sources are inorganic nitrogen sources such as ammonium nitrate, ammonium sulfate, ammonium chloride, ammonium phosphate, sodium nitrate, and the like; and organic nitrogen sources such as soybean flour, corn steep liquor, casamino acid, yeast extract, meat extract, peptone, cotton seed meal, Cultivator, Ajix, sodium glutamate, and the like.

Given as examples of carbon sources are fibrous substances such as chaff, hull, sawdust; CMC, Avicel, cellulose cotton, xylan, pectin, as well as assimilable carbon sources such as arabinose, xylose, glucose, mannose, fructose, galactose, sucrose, trehalose, and glycerol; and assimilable organic acids such as citric acid, acetic acid, and the like. In addition to these carbon and nitrogen sources, phosphoric acid, inorganic salts of $Mg^{2+}$, $Ca^{2+}$, $Na^+$, $K^+$, and the like, and as required, other micronutritious organic or inorganic substances can be added into the culture medium.

Collection and purification of proteinase-resistant cellulase from the culture broth may be carried out by means of conventional collection and purification methods adapted to general enzymes. If necessary, a proteinase treatment according to a method described hereinafter may be performed with the utilization of the proteinase-resistance of the enzyme.

Specifically, cells are separated from the culture broth by means of centrifugation, filtration, or the like to obtain a crude enzyme liquid. Although it is possible to use the crude enzyme liquid thus obtained as is, enzyme powder may be obtained, if required, by concentration by means of separation methods, such as, salting out, precipitation from a solvent (e.g. methanol, ethanol, isopropyl alcohol) to precipitate proteins, ultrafiltration (e.g. by using the ultrafilter with a fraction molecular weight of 13,000, manufactured by Asahi Chemical Co., Ltd.) and the like, followed by freeze-drying. The salting out is performed, for example, by precipitating the enzyme from ammonium sulfate (60–100% saturation fraction), followed by filtration or centrifugation, desalination, and freeze-drying. For the desalination, a commonly used method such as dialysis, gel permeation using Sephadex G-25 (a product of Pharmacia), or the like is used. Furthermore, proteinase-resistant cellulase can be separated and purified by a suitable combination of the proteinase treatment, ion-exchange chromatography, molecular sieve chromatography, and the like.

The proteinase-resistant cellulase produced by *Aspergillus niger* KSM-24 has enzymological characteristics discussed below.

Enzymatic activities were measured by using the following buffer solutions according to the method explained below.

Buffer Solutions pH 2–3: glycine-HCl buffer
pH 3–6: sodium citrate buffer
pH 6–8: sodium phosphate buffer
pH 8–11: glycine-NaOH buffer Measurement of Enzymatic Activities (1) CMC-ase activity The enzyme solution (0.1 ml) was added to 0.9 ml of substrate solutions each containing 10 mg of CMC (A01MC: trademark, manufactured by Sanyo-Kokusaku Pulp Co., Ltd.) and one of the above-buffer solutions at a concentration of 100 mM, and reacted at 40° C. for 20 minutes. On completion of the reaction, reducing sugar was quantitatively analyzed by the 3,5-dinitrosalicylic acid (DNS) method. Specifically, 1.0 ml of DNS reagent was added to 1.0 ml of the reaction liquid, and the mixture was caused to color by heating at 100° C. for 5 minutes. After cooling, the colored mixture was diluted with 4.0 ml of distilled water and subjected to colorimetry at 535 nm. One (1) unit of enzyme titer is defined as the amount of the enzyme producing reducing sugars corresponding to 1 μmol of glucose per minute.

(2) p-Nitrophenylcellobioside-resolving activity

A suitable amount of enzyme liquid was reacted at 40° C. in 1.0 ml of a reaction liquid containing 0.1 μmol of p-nitrophenylcellobioside (manufactured by Sigma Co.) and 100 mM sodium citrate buffer (pH 5). 1 N $Na_2CO_3$ (0.3 ml) and distilled water (1.7 ml) were added in this order and the free p-nitrophenol was colorimetrically analyzed at 400 nm. One (1) unit of enzyme titer is defined as the amount of the enzyme producing 1 μmol of free p-nitrophenol per minute.

(3) Avicel-, cellulose powder-, phosphoric acid swollen cellulose-, and filter paper-resolving activity A suitable amount of enzyme liquid was added to 2.0 ml of a reaction liquid containing 15 mg of Avicel (manufactured by Merc Co.) and 100 mM sodium citrate buffer (pH 5) and reacted at 40° C. with shaking. After the reaction, the mixture was centrifuged (3,000 rpm) at 5° C. for 20 minutes. The supernatant (1.0 ml) was subjected to quantitative analysis of reducing sugars by the 3,5-dinitrosalicylic acid (DNS) method.

Other enzymatic activities were measured in the same manner as above. Cellulose powder (manufactured by Toyo Roshi Co.) was used for the cellulase powder resolvingactivity test; cellulose treated by the method of Tomita et al. (Tomita, Y. et al., *J. Ferment. Technol.*, 52, 235, 1974) was used for the determination of the phosphoric acid swollen cellulose-resolving activity, and filter paper (Toyo No. 51-Toku: trademark, manufactured by Toyo Roshi Co.) was used in the filter paper-resolving activity determination. One (1) unit of enzyme titer is defined as the amount of the enzyme producing reducing sugar corresponding to 1 μmol of glucose per minute.

(4) Cellobiase activity

A suitable amount of enzyme liquid was added to 1.0 ml of a reaction liquid containing 10 mg of cellobiose (manufactured by Toyo Chemical Co.) and 100 mM sodium citrate buffer and reacted at 40° C. The enzyme was deactivated at 100° for 10 minutes to determine the amount of glucose produced by the Mutarotase method using Glucose C-Test kit (a product of Wako Pure Chemicals Co., Ltd.). One (1) unit of enzyme titer is defined as the amount of the enzyme producing 2 μmol of glucose per minute.

Enzymological characteristics (1) Action

Exhibits significant activity on carboxymethyl cellulose (CMC) and dissolves CMC producing reducing sugars such as glucose.

(2) Substrate specificity

Beside CMC, exhibits some degree of activity on phosphoric acid-swollen cellulose and amilose. Does not exhibit resolving activities on crystalline fibers (e.g. Avicel, cellulose powder, filter paper), and on p-nitrophenylcellobioside and cellobiose.

(3) Working pH range and optimum pH

Has a wide working pH range of 3-10 and an optimum pH of 6.0. At pH 4-8, maintains the relative activity 50% or more of the relative activity at optimum pH (FIG. 1)

(4) Stable pH range

Figure 2:
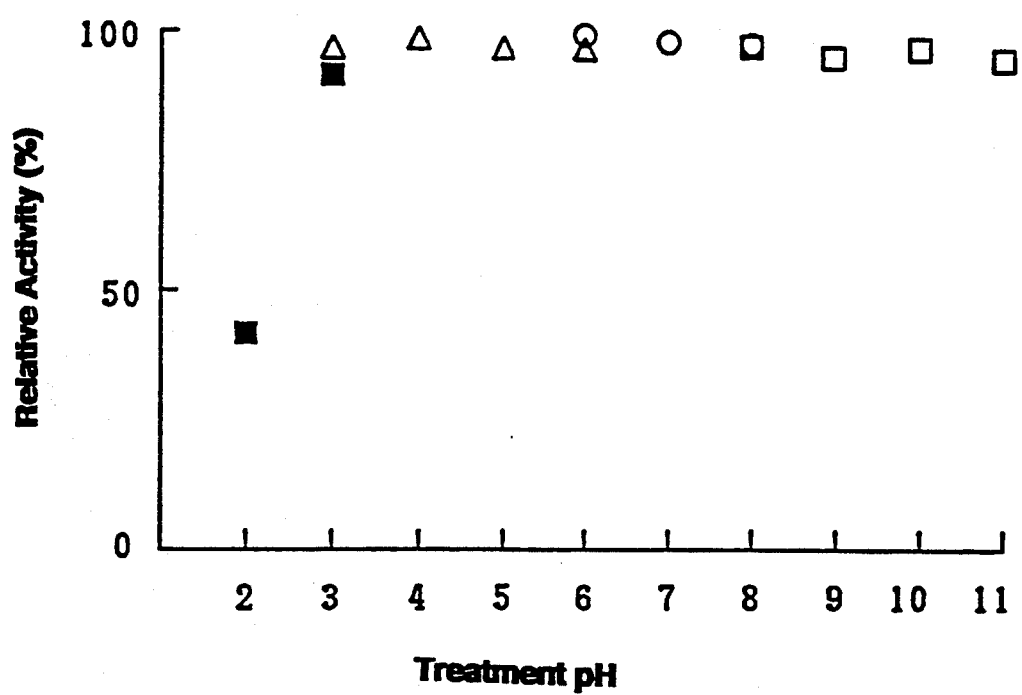
FIG. 2 shows the relationship between the treatment pH and the relative activity of the proteinase-resistant cellulase measured in a glycine-NaOH buffer solution (open squares), a sodium citrate buffer solution (open triangles), a sodium phosphate buffer solution (open circles), and a glycine-HCl buffer solution (solid squares).

Remains stable over a wide pH range of 3-11 when allowed to stand at 30° C. for 1 hour (FIG. 2).

(5) Working temperature range and optimum temperature

Figure 3:
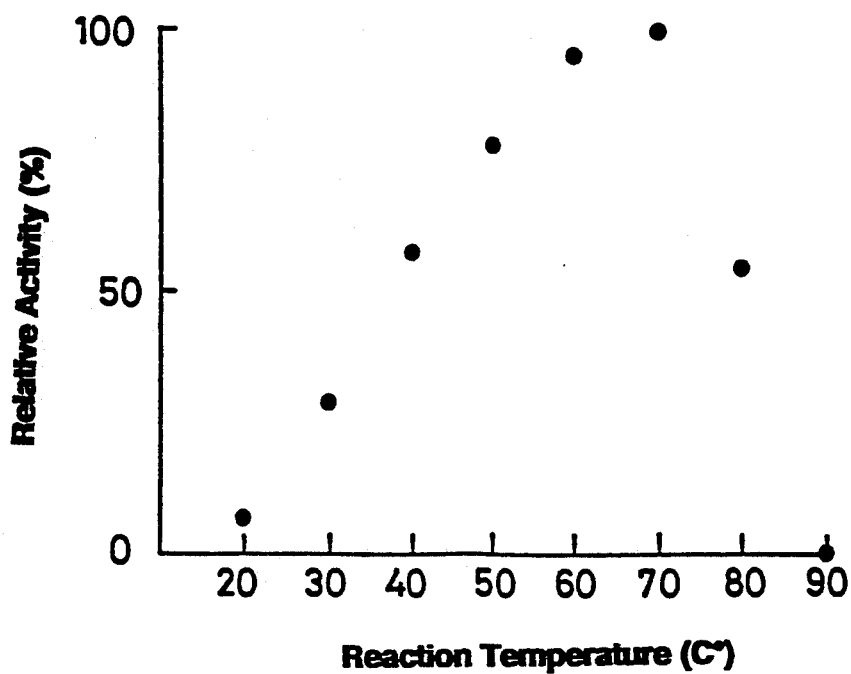
FIG. 3 presents the relationship between the reaction temperature and the relative activity of the proteinase-resistant cellulase.

Works over a wide temperature range of 20°-85° C., when measured in 100 mM glycine-NaOH buffer solution (pH 9), with the optimum temperature being 70° C. At 40°-80° C., maintains the relative activity of 50% or more of the relative activity at the optimum temperature (FIG. 3).

(6) Temperature stability

Figure 4:
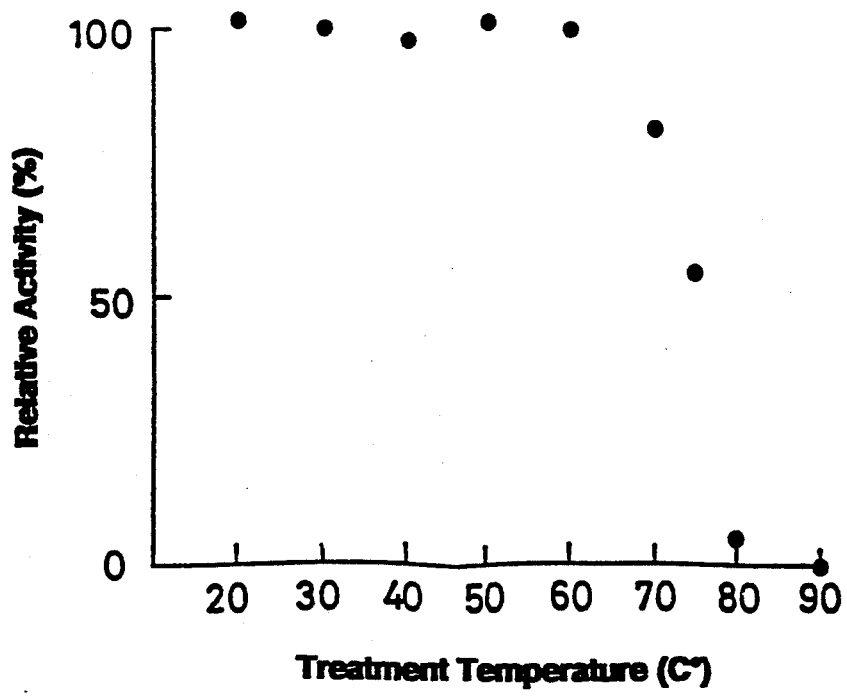
FIG. 4 is the relationship between the treatment temperature and the relative activity of the proteinase-resistant cellulase.

The relative activity of the enzyme treated at various temperatures in 100 mM glycine-NaOH buffer solution (pH 9) for 10 minutes is shown in FIG. 4. The enzyme was active at 60° C. and maintained 50% or more residual activity at 75° C.

(7) Effects of chelating agents

The activity of the enzyme in the presence of EDTA, EGTA, NTA, and STPP was measured, and was not found to be substantially inhibited by these chelating agents.

(8) Effects of metallic ion

The effects of various metallic ions ($Al^{3+}$, $Fe^{3+}$, $Ba^{2+}$, $Ca^{2+}$, $Co^{2+}$, $Cu^{2+}$, $Fe^{2+}$, $Hg^{2+}$, $Mg^{2+}$, $Mn^{2+}$, $Ni^{2+}$, $Sn^{2+}$, and $Zn^{2+}$ at a concentration of 1 mM, and $K^+$ and $Na^+$ at 0.5 mM) on the activity of the enzyme were examined and found to be inhibited by $Cu^{2+}$, $Sn^{2+}$, and $Hg^{2+}$.

(9) Molecular weight

The molecular weight of the enzyme measured by the gel permeation method using TSK-G2000SW (a product of Toso Co.) was about 60,000, and by the SDS-polyacrylamide electrophoresis method using Phast-system (a product of Pharmacia) was about 52,000.

(10) Sugar content

The sugar content was measured by the phenol-sulfuric acid method and the enzyme was found to contain about 9% (as mannose) of sugars.

(11) Resistance to surface active agents

The enzyme was allowed to stand in 10% aqueous solutions of linear alkylbenzenesulfonic acid (LAS), sodium alkylsulfonate (SAS), sodium alkylsulfate (AS), and sodium polyoxyethylenealkylsulfate (ES) at 40° C. for 2 weeks to measure its residual activity. As shown in Table 1, the residual activity was found to be 50% or more after 2 weeks in any tested surface active agents.

TABLE 1

| Surface Active Agent | Residual Activity (%) | |
|---|---|---|
| | After 1 week | After 2 weeks |
| Not added * | 97 | 97 |
| LAS | 81 | 52 |
| SAS | 75 | 61 |
| AS | 65 | 62 |
| ES | 98 | 72 |

* 100 mM glycine buffer (pH 9)

(12) Proteinase-resistance

To investigate the stability of the enzyme, 1 AU/ml of proteinase, e.g., Savinase (Novo), Pepsin (Sigma) or Papain (Sigma) was added to 100 mM phosphate buffer (pH 7). The solution was kept at 40° C. for two weeks and its residual activity was measured. The enzyme of this invention exhibited strong resistance against proteinase with 50% or more of residual activity (see Table 2).

TABLE 2

| Proteinase | Residual Activity (%) | |
|---|---|---|
| | After 1 week | After 2 weeks |
| Not added | 97 | 97 |
| Savinase | 83 | 76 |
| Pepsin | 86 | 75 |
| Papain | 81 | 78 |

Other features of the invention will become apparent in the course of the following description of the exemplary embodiments which are given for illustration of the invention and are not intended to be limiting thereof.

EXAMPLES

Example 1

About 1 g of soil collected from around Kamisu-machi, Kashima-gun, Ibaraki-ken, Japan was suspended in 5 ml of sterilized water of 1% NaCl content and the suspension was stirred and left to stand. The supernatant was applied onto an isolating agar medium which contained CMC (Medium 1), and cultured at 30° C. for 2-7 days to grow colonies. The colonies which formed halo were collected to obtain CMC-ase-producing strains. The cells were subjected to the SCI treatment repeatedly until they became pure through naked eye and microscopic observation and thus obtained strictly pure microorganism. The microorganism obtained was further inoculated into the Liquid Medium 2 and shake-cultured at 30° C. for 3 days. After the cultivation, the cultured broth was centrifuged to separate a supernatant. To the supernatant were added 1% ES and Savinase (Novo) to bring it 1 AU/ml and stored at 40° C.

The residual CMC-ase activity of the supernatant was measured at pH 9 to select the proteinase-resistant cellulase-producing strains. *Aspergillus niger* KSM-24 (FERM BP-3359) was thus obtained.

|  | % by weight |
|---|---|
| Medium 1: CMC-containing agar medium | |
| CMC | 3 |
| $NaNO_3$ | 0.1 |
| $KH_2PO_4$ | 0.1 |
| $MgSO_4 \cdot 7H_2O$ | 0.05 |
| Yeast extract | 0.05 |
| Agar | 1 |
| (30 ppm of Streptomycin was added) | |
| Medium 2: | |
| CMC | 1.0 |
| Polypeptone | 0.5 |
| Yeast extract | 0.05 |
| $KH_2PO_4$ | 0.1 |
| $MgSO_4 \cdot 7H_2O$ | 0.02 |

Example 2

The *Aspergillus niger* KSM-24 strain was inoculated into the Liquid Medium 2 of Example 1 which was slightly modified by adding 3% wheat bran instead of CMC and 0.5% nitric acid instead of polypeptone, and shake-cultured at 30° C. for 3 days with 0.5 vvm aeration and 200 rpm stirring in a 30 l fermenter. After cultivation, the cells and the insolubles were removed by means of filter press to obtain a crude enzyme. 15 l of the crude enzyme was concentrated and desalted by means of ultra-filtration (Asahi Kasei, fractional molecular weight 13,000) to prepare one (1) liter of the crude enzyme liquid. The crude enzyme liquid was further freeze-dried to obtain 17.2 gm of the proteinaseresistant enzyme as dry powders (specific activity* 110 unit/gm).

* The enzymatic activity was measured at pH 9. Example 3 and Comparative Example 1

The crude enzyme prepared in Example 2 was mixed with 10% ES and 1 AU/ml Savinase and left to stand for 2 weeks at 40° C. to examine the residual activity. The residual activity of the enzyme was confirmed to be 63%.

A commercially available cellulase (manufactured by ICN Biochemical, derived from *Aspergillus niger*) was also examined in the same manner and confirmed that the residual activity was 5%.

Example 4

One (1) gm of the dry powder prepared in Example 2 was dissolved into 10 ml of 50 mM glycine-NaOH buffer (pH 9) and purified by the following procedure.

(1) 0.5 AU/ml Savinase was added to the admixture of the enzyme liquid. The mixture was processed for 24 hours at 40° C. to decompose the contaminating protein other than proteinase-resistant cellulase.

(2) The treated proteinase solution was exchanged to a phosphate buffer (pH 6) by means of ultra-filtration (product of Amicon, fractional molecular weight 10,000).

(3) The solution was then adsorbed to TSK-DEAE3SW column [product of Toso, equilibrated by 50 mM phosphate buffer (pH 6)] and eluted by increasing the NaCl concentration linearly from 0 to 0.3 M.

(4) The active fraction obtained in (3) was concentrated by means of ultra-filtration and exchanged to glycine buffer (pH 9).

(5) The solution obtained in (4) was then adsorbed to TSK-DEAE5PW column [product of Toso, equilibrated by 50mM glycine buffer (pH 9)] and eluted by increasing the NaCl concentration linearly from 0 to 0.5 M.

(6) The active fraction obtained in (5) was fractionated by gel-permeation chromatography using TSK-G20003SW column (product of Toso) and the proteinase-resistant cellulase was eluted at the position of approximately 60,000 molecular weight.

(7) The fraction obtained in (6) was subjected to polyacrylamide gel electrophoresis applying the Phast-system (a product of Pharmacia) and stained with Coomassie Brilliant Blue and silver to confirm that it gave a single band.

Example 5

The enzyme obtained in Example 4 was subjected to SDS-polyacrylamide gel electrophoresis applying the Phast-system (a product of Pharmacia) and was confirmed that the proteinase-resistant cellulase had a molecular weight of approximately 52,000. (see FIG. 5)

Example 6

About 1 g of soil collected from around Hasakimachi, Kashima-gun, Ibaraki-ken, Japan was suspended in 1% sterilized water and the suspension was stirred and left to stand. The supernatant was applied onto an isolating agar medium which contained CMC (Medium 1), and cultured at 30° C. for 2–7 days to grow colonies. The colonies which formed halo were collected to obtain CMC-ase-producing strains. The cells were subjected to the SCI treatment repeatedly until they became pure through naked eye and microscopic observation and thus obtained strictly pure microorganism. The microorganism obtained was further inoculated into the Liquid Medium 2 and shake-cultured at 30° C. for 3 days. After the cultivation, the cultured broth was centrifuged to separate a supernatant. To the supernatant were added 1% Sodium polyoxyethylenealkyl sulfate (ES) and Savinase (Novo) to bring it 1 AU/ml and stored at 40° C. The residual CMC-ase activity of the supernatant was measured at pH 9 and the proteinase-resistant cellulase-producing strain was selected *Aspergillus niger* KSM-25 (FERM BP-3360 was thus obtained.

Example 7

The *Aspergillus niger* KSM-25 strain obtained in Example was inoculated into the Liquid Medium 2 of Example 1 which was slightly modified by adding 3% wheat bran instead of CMC and 0.5% nitric acid instead of polypeptone, and shake-cultured at 30° C. for 3 days with 0.5 vvm aeration and 200 rpm stirring in a 30 l fermenter. After cultivation, cells and insoluble were removed by means of filter press to obtain a crude enzyme liquid. 15 l of the crude enzyme liquid was concentrated and desalted by means of ultrafiltration (product of Asahi Kasei, fractional molecular weight 13,000) to prepare one (1) liter of the concentrated crude enzyme liquid. The crude enzyme liquid was further freeze-dried to obtain 18.6 gm of the proteinase-resistant enzyme as dry powders(specific activity* 105 unit/gm).

* The enzymatic activity was measured at pH 9.

Example 8

The crude enzyme prepared in Example 7 was mixed with 10% ES and 1 AU/ml Savinase and left to stand for 2 weeks at 40° C. to examine the residual activity. The residual activity of the enzyme was confirmed to be 63%.

Example 9

The microorganism isolated from the soil and that obtained from the microorganism depositary organization were inoculated together on Liquid Medium 2 and shake-cultured at 30° C. for three days. After the cultivation, the cultured broth was centrifuged to separate a supernatant. To the supernatant were added 1% ES and 1 AU/ml Savinase (Novo) and stored at 40° C. The residual CMC-ase activity of the supernatant was measured at pH 9 to select the proteinase-resistant cellulase-producing strains.

By the above-mentioned procedures, *Aspergillus niger* IFO-31125 obtained from Fermentation Institute was confirmed to produce the proteinase-resistant cellulase of this invention.

Example 10

The *Aspergillus niger* IFO-31125 strain obtained in Example 9 was inoculated into the Liquid Medium 2 of Example 1 which was slightly modified by adding 3% wheat bran instead of CMC and 0.5% nitric acid instead of polypeptone, and shake-cultured at 30° C. for 3 days with 0.5 vvm aeration and 200 rpm stirring in a 30 l fermenter. After the cultivation, the cells and the insolubles were removed by means of filter press to obtain a crude enzyme liquid. 15 l of the crude enzyme liquid was concentrated and desalted by means of ultra-filtration (product of Asahi Kasei, fractional molecular weight 13,000) to prepare one (1) liter of the concentrated crude enzyme liquid. The crude enzyme liquid was further freeze-dried to obtain 2.1 gm of the proteinase-resistant enzyme as dry powders (specific activity 500 unit/gm).

Example 11

The crude enzyme liquid prepared in Example 10 was mixed with 10% ES and 1 AU/ml Savinase and left to stand for 2 weeks at 40° C. to examine the residual activity. The residual activity of the enzyme was confirmed to be 55%.

Example 12

One (1) gm of the dry powders prepared in Example 10 was dissolved into 10 ml of 50 mM glycine-NaOH buffer (pH 9) and purified by the following procedures.

(1) Savinase was added to the solution of the enzyme to a concentration of 0.5 AU/ml. The mixture was processed for 24 hours at 40° C. to decompose the contaminating protein other than the proteinase-resistant cellulase.

(2) The treated proteinase solution was exchanged to a phosphate buffer (pH 6) by means of ultra-filtration product of Amicon, fractional molecular weight 10,000).

(3) The solution was then adsorbed to TSK-DEAE3SW column [product of Toso, equilibrated by 50 mM phosphate buffer (pH 6)] and eluted by increasing the NaCl concentration linearly from 0 to 0.3 M.

(4) The fractions between 98-110 obtained in (3) were concentrated by means of ultra-filtration and exchanged to glycine buffer (pH 9).

(5) The solution obtained in (4) was then adsorbed to TSK-DEAE5PW column [product of Toso, equilibrated by 50 mM glycine buffer (pH 9)] and eluted by increasing the NaCl concentration linearly from 0 to 0.5 M.

(6) The fractions between 30-36 obtained in (5) were fractionated by gel-permeation chromatography using TSK-G20003SW column (product of Toso) and the proteinase-resistant cellulase was eluted at the position of approximately 40,000 molecular weight.

(7) The fractions obtained in (6) were subjected to polyacrylamide gel electrophoresis applying the Phast-system (a product of Pharmacia) and stained with Coomassie Brilliant Blue and Silver to confirm that it gave a single band.

Example 13

The enzyme obtained in Example 12 was subjected to SDS-polyacrylamide gel electrophoresis applying the Phast-system (a product of Pharmacia) and was confirmed that the proteinase-resistant cellulase had a molecular weight of approximately 42,000.

Obviously, numerous modifications and variations of the present invention are possible in light of the above teachings. It is therefore to be understood that within the scope of the appended claims, the invention may be practiced otherwise than as specifically described herein.

What is claimed is:

1. A cellulase which maintains its residual activity of 50% or more after two weeks when stored at 40° C. in the presence of 1 AU/ml proteinase and which possesses the following physicochemical characteristics:

(1) Action

Dissolves carboxymethyl cellulose (CMD) producing reducing sugars;

(2) Substrate specificity

Beside CMC, dissolves phosphoric acid-swollen cellulose and amilose;

(3) Working pH range and optimum pH

Has a working pH range of 3-10 and an optimum pH of 6;

(4) Stable pH range

Remains active when allowed to stand at 30° C. for 1 hour in a pH range of 3-11;

(5) Working temperature range and optimum temperature

Works in a wide temperature range of 20°-85° C., with the optimum temperature being 70° C.;

(6) Temperature stability

Maintains activity when allowed to stand at 60° C. for 10 minutes and 50% or more activity when allowed to stand at 75° C. for 10 minutes;

(7) Effects of chelating agents

The activity is not inhibited by EDTA, EGTA, NTA, and STPP;

(8) Effects of metallic ion

The activity is inhibited by $Cu^{2+}$, $Sn^{2+}$, and $Hg^{2+}$;

(9) Molecular weight

Has a molecular weight of about 60 when measured by the gel permeation method;

(10) Sugar content

Contains about 9% of sugars when measured by the phenol-sulfuric acid method; and

(11) Resistance to surface active agents

Maintains the residual activity of 50% or more after two weeks when stored at 40° C. together with a 10% aqueous solution of linear alkylbenzenesulfonic acid, sodium alkylsulfonate, sodium alkylsulfate, or sodium polyoxyethylenealkylsulfate.

* * * * *

UNITED STATES PATENT AND TRADEMARK OFFICE
CERTIFICATE OF CORRECTION

PATENT NO. : 5,258,297
DATED : NOVEMBER 2, 1993
INVENTOR(S) : SHUN-ICHI AKIBA ET AL

It is certified that error appears in the above-identified patent and that said Letters Patent is hereby corrected as shown below:

Column 12, line 32, "CMD" should read --CMC--;
          line 57, "60" should read --60 kD--.

Signed and Sealed this

Fifth Day of July, 1994

Attest:

BRUCE LEHMAN

Attesting Officer    Commissioner of Patents and Trademarks